United States Patent [19]

Kaiser et al.

[11] 4,377,535

[45] Mar. 22, 1983

[54] PROCESS FOR THE PREPARATION OF NITRO-T-ACID (8-NITRO-NAPHTHALENE-1,3,6-TRISULPHONIC ACID)

[75] Inventors: Reinhard Kaiser, Cologne; Horst Behre, Odenthal; Jürgen Dammann, Cologne; Rolf Pütter, Duesseldorf; Axel Vogel, Odenthal, all of Fed. Rep. of Germany

[73] Assignee: Bayer Aktiengesellschaft, Leverkusen, Fed. Rep. of Germany

[21] Appl. No.: 219,615

[22] Filed: Dec. 24, 1980

Related U.S. Application Data

[63] Continuation of Ser. No. 64,960, Aug. 8, 1979, abandoned.

[30] Foreign Application Priority Data

Aug. 28, 1978 [DE] Fed. Rep. of Germany ....... 2837498

[51] Int. Cl.³ ..................... C07C 143/55; C07B 11/00
[52] U.S. Cl. ................................. 260/505 C; 260/688
[58] Field of Search ....................... 260/505 R, 505 C

[56] References Cited

FOREIGN PATENT DOCUMENTS 56058 of 1896 Fed. Rep. of Germany .

OTHER PUBLICATIONS

Kirk–Othmer "Encyclopedia of Chemical Technology", vol. 13, p. 716, (1967), Interscience, Publ. TP9.E68.

"Ullmanns Encyklopaedie der technischen Chemie", vol. 12, pp. 630–631 (1960), TP9.U6.

"Hackh's Chemical Dictionary", 4th Ed. (1969), p. 457.

*Primary Examiner*—Natalie Trousof
*Assistant Examiner*—L. Hendriksen
*Attorney, Agent, or Firm*—Sprung, Horn, Kramer & Woods

[57] ABSTRACT

A process has been provided for the preparation of nitro-T-acid by nitration of naphthalene-1,3,6-trisulphonic acid from a nitration mixture which has reacted to the extent of at least 80% which naphthalene-1,3,6-trisulphonic acid or a mixture containing the latter. Nitro-T-acid (and T-acid) is an intermediate for the preparation of H-acid which, in turn, is an intermediate for the preparation of dyestuffs.

1 Claim, No Drawings

PROCESS FOR THE PREPARATION OF NITRO-T-ACID (8-NITRO-NAPHTHALENE-1,3,6-TRISULPHONIC ACID)

This is a continuation of application Ser. No. 64,960, filed Aug. 8, 1979 now abandoned.

The present invention relates to a process for the preparation of nitro-T-acid by nitration of naphthalene-1,3,6-trisulphonic acid.

It is known to prepare nitro-T-acid by nitrating the isomer mixture of naphthalenetrisulphonic acids, which is obtained by trisulphonation of naphthalene with sulphuric acid and oleum and contains naphthalene-1,3,6-trisulphonic acid as the main constituent, by means of nitric acid in sulphuric acid as the solvent (see German Reich Pat. No. 56,058 and F.I.A.T., Final Report 1,016, pages 32 to 39).

The procedures which follow covering 1. sulphonation and 2. nitration are translations of material found in FIAT Final Report No. 1016, pages 37 and 38:

1. Sulphonation:
   1000 kg naphthalene (m.p. 79.8°–79.9°)
   2265 kg sulphuric acid monohydrate
   2860 kg 65% oleum Sulphonation is carried out in a 5400 l cast iron stirrer vessel with a jacket for 10 atm. vapour pressure and water cooling. 20 h.p. motor with a coupling for 20 and 70 revolutions per minute. 1000 kg naphthalene are introduced caskwise into 1300 kg sulphuric acid monohydrate which has already been placed in the vessel and has been cooled to 20° C. Then the reaction mixture is heated to 80°–85° and kept at this temperature for one hour. Then it is heated up to 145° C. After cooling to 85° C. the mixture is diluted with 965 kg sulphuric acid monohydrate and sulphonation is then continued at 40° C. using 65% oleum. 2560 kg 65% oleum are first added in the course of 8 hours, then the reaction mixture is heated to 145° C. and kept at this temperature for 2½ hours. After the reaction mixture has been cooled to 60° a further 300 kg 65% oleum are added at this temperature and the mixture is heated for 2–3 hours to 150°–155° C. After cooling to 100° 400 liters of water are added in the course of one hour. The reaction product is transferred under pressure to the nitration vessel.

2. Nitration:
   690 kg mixed acid H Acid
   (mixed acid H Acid=86% HNO₃)
   (18–20% excess HNO₃)

Nitration is carried out in a 4500 liter cast iron reactor with a gate paddle agitator which revolves 70 times per minute. The sulphonation (product) diluted with water as described above is nitrated within 10 hours at 35°–40° C. with 690 kg mixed acid H Acid. The excess nitric acid is removed by introducing the finished batch within two hours into 200–2700 liters of washing effluent as obtained in the last washing of the gipsum which washing effluent is in a lead-coated cast steel reactor lined with an acidic stone material. The temperature rises up to 103° C. The nitrose fumes leave at a rate proportionate to the introduction of the starting product for nitration; they are washed with sulphuric acid in an absorber made of ferrosilicon and then passed to the inorganic department for processing into HNO₃.

In the methods of preparation known from the literature, the procedure followed is that the solution of naphthalenetrisulphonic acids in sulphuric acid, which is obtained on trisulphonation of naphthalene and is at 150° to 155° C., is cooled to 100° C., diluted with water and further cooled to 80° C. The batch is then transferred into the nitration kettle, cooled therein to 35°–40° C., and nitrated in the course of about 10 hours with 86% strength nitric acid (12% of sulphuric acid, 2% of water) at 35° to 40° C. The heat of reaction is removed through the kettle wall by cooling with cooling water.

There has now been found a process for the preparation of 8-nitronaphthalene-1,3,6-trisulphonic acid from naphthalene-1,3,6,-trisulphonic acid, or from mixtures containing the latter, by nitration with nitric acid in sulphuric acid, which is characterised in that a nitration mixture which has reacted to the extent of at least 80% is taken, naphthalene-1,3,6-trisulphonic acid or mixtures containing the latter, dissolved in sulphuric acid, are added, at the same time 1.0 to 1.4 mols of nitric acid per mol of naphthalene (present in the form of naphthalenesulphonic acid) and, if appropriate, water are added so that a sulphuric acid concentration in the range of 86 to 94% by weight (of sulphuric acid, relative to the sum of all the water present and sulphuric acid) is maintained during the nitration, the reaction mixture is mixed thoroughly and the reaction temperature is kept in the range from 30° to 60° C.

Pure naphthalene-1,3,6-trisulphonic acid, dissolved in sulphuric acid, can be employed in the process according to the invention. It is also possible to employ mixtures containing naphthalene-1,3,6-trisulphonic acid, dissolved in sulphuric acid. Preferably, mixtures containing naphthalene-1,3,6-trisulphonic acid, dissolved in sulphuric acid, such as are obtained from the trisulphonation of naphthalene, are employed. For example, it is possible to use the mixture which is obtained on trisulphonation of naphthalene according to F.I.A.T., Final Report, loc. cit. The mixture prepared in this manner contains, in about 100% strength sulphuric acid, about 40 to 48% by weight of naphthalenetrisulphonic acids, of which about 75% by weight is naphthalene-1,3,6-trisulphonic acid, about 8% by weight is naphthalene-1,3,5-trisulphonic acid and about 12% by weight is naphthalene-1,3,7-trisulphonic acid. In addition to sulphuric acid and naphthalenetrisulphonic acids, the mixture can also contain small amounts of other sulphonation products of naphthalene and/or oxidation products of naphthalene. Naphthalenetrisulphonic acid mixtures prepared by other methods can also be employed in the process according to the invention.

Since the solubility of the naphthalenetrisulphonic acids and especially of naphthalene-1,3,6-trisulphonic acid in 100% strength sulphuric acid at room temperature is low, preferably solutions which are at a temperature between 100° and 200° C. are used for introduction into the process according to the invention. In general, the solutions which can be obtained directly from the trisulphonation of naphthalene and which are, for example, at a temperature in the range from 140° to 160° C. are very suitable.

The nitration mixture first introduced into the reactor can, for example, have reacted to the extent of at least 80%, preferably to the extent of at least 90%. It is particularly preferred to take a nitration mixture which has reacted to the extent of 95–99%. In discontinuous operation, a part of the preceding batch can be taken, whilst in continuous operation the procedure can be to introduce naphthalene-1,3,6-trisulphonic acid and nitric acid into a loop reactor (compare Ullmann Enzyklopädie der technischen Chemie (Ullmann, Encyclopaedia of industrial Chemistry), Verlag Chemie, Weinheim/Bergstr., volume 1, page 227 and volume 4, page 9) in which the nitration mixture is nitrated to the extent of at least 80%, preferably to the extent of at least 90%, and very particularly preferentially to the extent of 95–99%, before the point of addition.

The amount of the sulphuric acid solution containing naphthalene-1,3,6-trisulphonic acid can, if the process according to the invention is carried out discontinuously, be, for example, 5 to 5,000% by weight, preferably 300 to 1,000% by weight, relative to the reacted nitration mixture initially introduced. Where the process according to the invention is carried out continuously, the amount of sulphuric acid solution containing naphthalene-1,3,6-trisulphonic acid which can be introduced into the recycled reaction mixture can be at most such that the amount of naphthalene-1,3,6-trisulphonic acid introduced is nitrated to the extent of at least 80%, preferably to the extent of at least 90%, in the first pass.

Simultaneously with the sulphuric acid solution containing naphthalene-1,3,6-trisulphonic acid, 1.0 to 1.4 mols of nitric acid per mol of naphthalene (present in the form of naphthalenesulphonic acids) are introduced into the process according to the invention. Preferably, this amount of nitric acid is 1.1 to 1.25 mols. The nitric acid can be added, for example, in the pure form (100% $HNO_3$) or in the form of aqueous nitric acid containing more than 60% by weight of $HNO_3$. For example, 60 to 100% strength nitric acid can be added. It is particularly preferred to use aqueous nitric acid of a concentration of 67 to 68% by weight (so-called azeotropic acid).

It is an essential feature of the process according to the invention that during the nitration the concentration of the sulphuric acid undergoes virtually no change, or only a slight change, and is in the range from 86 to 94% (of sulphuric acid, relative to the sum of water and sulphuric acid). Preferably, the sulphuric acid concentration is in the range from 88 to 92%. This concentration can be influenced by the water liberated during the reaction, by the water which may be introduced with the nitric acid, or by water which may be added separately. In order to obtain and maintain the desired concentration of sulphuric acid it is therefore necessary precisely to control the amount of water present in the nitration mixture. The required sulphuric acid concentration can be obtained by adding the necessary amount of water together with the nitric acid or separately therefrom. Surprisingly, it has been found that in most cases a suitable sulphuric acid concentration is obtained if the nitric acid is added in the form of aqueous nitric acid having a concentration of 67 to 68% by weight (so-called azeotropic acid), in an amount of 1.1 to 1.25 mols per mol of naphthalene (present in the form of naphthalenesulphonic acids), and if no additional water is added. If it is desired to employ more highly concentrated nitric acid, it is in general necessary additionally to feed in an appropriate amount of water.

The temperature of the nitric acid added and, where relevant, the temperature of the water added are of no particular importance. For example, nitric acid and, where relevant, water which are at room temperature can be employed.

It is furthermore essential for the process according to the invention that the nitration mixture should be thoroughly mixed with the reactants. For this, customary apparatus can be used, for example high-speed stirrers when working in a stirred kettle, or loop reactors when working continuously. The thorough mixing of the nitration mixture with the reactants is necessary in order to avoid local overheating of the reaction mixture.

The pressure at which the process according to the invention is carried out is without special importance. Preferably, it is carried out under normal pressure, but it can also be carried out under elevated or reduced pressure. Furthermore, it can be carried out in the presence of an inert gas, for example nitrogen.

The reaction temperature, in the process according to the invention, must be maintained in the range from 30° to 60° C. Preferably, the range of 35° to 45° C. is used. In order to be able to maintain these temperatures it is necessary to conduct away, within a short space of time, the heat of reaction, the heat of dilution and the heat to be removed in order to cool the sulphuric acid solution containing naphthalene-1,3,6-trisulphonic acid. This heat can be conducted away through the container walls and/or through cooling coils immersed in the reaction mixture. It has proved particularly advantageous to employ an external heat exchanger through which the nitration mixture is circulated by pumping during the nitration, and in which it is cooled by indirect cooling by means of cooling water.

The process according to the invention can be operated discontinuously or continuously. In discontinuous operation it is possible to use, for example, a stirred vessel as the reactor. In continuous operation, it is possible to use several reactors, for example 2 to 3 reactors, which are operated in continuous succession, the nitration being carried out to a large extent, for example to the extent of at least 80%, preferably to the extent of at least 90%, in the first reactor. The nitration can then be completed in the second reactor. If required, a third reactor can also be present. Preferably, the process according to the invention is carried out continuously. In that case, the first reactor is preferably a loop reactor and the second reactor and, where present, the third reactor are preferably stirred kettles. The heats to be removed in the loop reactor are preferably removed by circulating the reactor contents, by pumping, over a heat exchanger located in the circuit.

In a preferred embodiment of the process according to the invention, in discontinuous operation, the method employed is as follows: an amount of reacted nitration mixture which allows the stirrer of the vessel to stir the mixture thoroughly is introduced into a vessel, for example, about 5 to 50% by volume of reacted nitration mixture is introduced into a vessel (based on the total volume of all components which are added). Thereafter, for example, 120 mol% of 67 to 68% strength aqueous nitric acid (so-called azeotropic acid) at a temperature of 20° to 25° C. and 100 mol% of a solution of naphthalenetrisulphonic acids in about 100% strength sulphuric acid, the solution having been prepared according to F.I.A.T., Final Report, loc. cit., and being at 140° to 160° C. are run in simultaneously through separate nozzles, whilst stirring rapidly, the speed of running in being such that a temperature of 35° to 38° C. is maintained in the reaction vessel. The heat of the reaction, the heat of dilution and heat to be removed in order to cool the hot sulphonation batch are conducted away by indirect cooling. After all has been run in, the mixture is allowed to react for a further 1 to 2 hours at 35° to 38° C.

In a preferred embodiment of the process according to the invention, carried out continuously, which embodiment can also preferentially be employed industrially, the method adopted is as follows: a naphthalenetrisulphonic acid mixture obtained according to F.I.A.T., Final Report, loc. cit., dissolved in about 100% strength sulphuric acid and containing about 33.8% of naphthalene-1,3,6-trisulphonic acid, about 5.8% of naphthalene-1,3,7-trisulphonic acid and about 3.7% of naphthalene-1,3,5-trisulphonic acid is metered, at a temperature of 150° to 160° C., together with a small amount of 100% strength sulphuric acid, into a loop reactor in which a nitration mixture which has reacted to the extent of about 95% is being rapidly circulated by means of a centrifugal pump. The sulphuric acid solution containing the naphthalenetrisulphonic acids is at the same time introduced into the loop reactor in such a way that rapid mixing of the hot sulphonation melt with the nitration mixture, and rapid cooling of the former by means of the latter, are ensured. At the same time about 68% strength aqueous nitric acid (azeotropic acid) is pumped into the loop reactor in a controllable ratio to the sulphuric acid containing naphthalenetrisulphonic acid, and is thoroughly mixed with the reactor contents. A temperature of 35° to 38° C. is obtained by cooling the circulated reactor contents with cooling water by means of a heat exchanger located in the circuit. After a mean residence time of about 20 to 40 minutes, the nitration mixture which has reacted to the extent of about 95% flows, via an overflow, into a stirred vessel in order to react there. In this vessel, the remaining heat of reaction can be removed by indirect cooling. After a further mean residence time of about 10–50 minutes, the nitration mixture which has virtually finished reacting flows into a third stirred kettle.

The mixture obtained after carrying out the process according to the invention can be worked up, for example, as described in F.I.A.T., Final Report, loc. cit., for example by diluting the mixture with water, driving off the nitrous fumes and removing the sulphuric acid present as calcium sulphate by adding calcium carbonate. The mixture thus obtained which essentially contains 8-nitronaphthalene-1,3,6-trisulphonic acid can then, without intermediate isolation of the said acid (nitro-T-acid) be used by convert the latter directly to T-acid by reducing the solution obtained with iron by the Bechamps method, or by catalytic hydrogenation. T-Acid can be separated out as the acid calcium-sodium salt, and can be isolated, by adding sodium chloride to the reduced solution and acidifying with hydrochloric acid (see in this context, for example, F.I.A.T., Final Report, loc, cit.).

Nitro-T-acid and T-acid are intermediate products for the preparation of H-acid, which in turn is an important intermediate product for the preparation of dyestuffs (see Ullmann, Enzyklopädie der technischen Chemie (Ullmann, Encyclopaedia of industrial Chemistry), 3rd edition, volume 12, page 621).

The nitration yields from the process according to the invention were determined as follows: water is first added to the nitration mixture which had finished reacting, then urea was added to remove dissolved nitrous fumes, thereafter the mixture was neutralised with sodium hydroxide solution, and then it was analysed by means of high pressure liquid chromatography.

If pure, virtually isomer-free naphthalene-1,3,6-trisulphonic acid dissolved in sulphuric acid is employed, about 96% of theory of 8-nitronaphthalene-1,3,6-trisulphonic acid (nitro-T-acid), about 3% of theory of 1-nitronaphthalene-2,5,7-trisulphonic acid and about 0.5% of theory of 2-nitronaphthalene-3,6,8-trisulphonic acid are obtained, corresponding to a total nitration conversion of 99.5% of theory.

If a mixture containing naphthalene-1,3,6-trisulphonic acid, dissolved in sulphuric acid, such as is obtained from the trisulphonation of naphthalene, is employed, then, for example when using a naphthalenetrisulphonic acid solution in about 100% strength sulphuric acid, containing about 33.8% of naphthalene-1,3,6-trisulphonic acid, about 5.8% of naphthalene-1,3,7-trisulphonic acid and about 3.7% of naphthalene-1,3,5-trisulphonic acid, about 96% of theory of nitro-T-acid, about 3% of theory of 1-nitronaphthalene-2,5,7-trisulphonic acid and about 0.5% of theory of 2-nitronaphthalene-3,6,8-trisulphonic acid was obtained as the nitration products of the naphthalene-1,3,6-trisulphonic acid. In that case, about 45% of theory of 1-nitronaphthalene-3,5,7-trisulphonic acid and about 7% of theory of 2-nitronaphthalene-3,5,7-trisulphonic acid are additionally obtained as nitration products of the naphthalene-1,3,7-trisulphonic acid, of which latter compound about 31% of theory remains un-nitrated. Furthermore, about 62% of theory of 1-nitronaphthalene-4,6,8-trisulphonic acid and about 8% of theory of 2-nitronaphthalene-4,6,8-trisulphonic acid are obtained as nitration products of naphthalene-1,3,5-trisulphonic acid, of which latter compound about 19% of theory remains un-nitrated.

The process according to the invention has a number of advantages over the processes known from the literature. Thus, the nitration reaction can be carried out with substantially shorter reaction times than hitherto. Furthermore, space/time yields of about 0.7 to 1 5 moles of nitro-T-acid per liter of vessel volume and per hour can be achieved, which is many times the space/time yield known from the literature. Because of the extraordinarily high space/time yields, the reactor volumes can be kept small, so that only a small stock of thermolabile, as yet undiluted nitration mixture is involved. As a result of the direct mixing of the sulphuric acid solution, containing naphthalene-1,3,6-trisulphonic acid, with the nitration mixture, and as a result of the rapid nitration reaction, the crystallising-out of naphthalenetrisulphonic acids is avoided. If the solution of naphthalenetrisulphonic acids in sulphuric acid obtained directly from the trisulphonation of naphthalene is employed, cooling of this sulphuric acid solution, which has hitherto been considered necessary, becomes superfluous. The reaction products are purer than in the previous processes and in particular fewer by-products which can delay or block the catalytic hydrogenation of nitro-T-acid to T-acid are formed. In contrast to the known processes, in which an 86% strength nitric acid, which contains 12% of sulphuric acid and 2% of water, is used, it is possible to employ the cheap 67 to 68% strength nitric acid (so-called azeotropic acid). Finally, the yields of nitro-T-acid, relative to naphthalene-1,3,6-trisulphonic acid, achievable with the process according to the invention are to be regarded as the optimum, since on virtually complete nitration of naphthalene-1,3,6-trisulphonic acid only 3 to 4% of unavoidable isomeric nitronaphthalenetrisulphonic acids are formed.

Though the nitration mixture is a supersaturated solution of nitro-T-acid in about 90% strength sulphuric acid and tends to crystallise, surprisingly no problems are encountered in carrying out the process according to the invention continuously.

EXAMPLES

Example 1

1,140 g of a nitration mixture which has reacted to the extent of about 95 to 99% and which has been prepared in accordance with F.I.A.T., Final Report, No. 1016, page 32 to 39, by nitrating the naphthalenetrisulphonic acid mixture from the trisulphonation of naphthalene with mixed acid (86% of nitric acid, 12% of sulphuric acid and 2% of water) are initially introduced, at 30° C., into a 2 l multineck flask equipped with a thermometer, stirrer, reflux condenser and 2 dropping funnels, and in the course of about 40 minutes 1,430 g of sulphonation melt (reaction mixture from the trisulphonation of naphthalene), which is at 150° to 160° C. and contains 33.8% by weight of naphthalene-1,3,6-trisulphonic acid, 5.8% by weight of naphthalene-1,3,7-trisulphonic acid and 3.7% by weight of naphthalene-1,3,5-trisulphonic acid as well as a small amount of naphthalene-1,3,5,7-tetrasulphonic acid and other sulphonation and sulphoxidation products, and 198 g of 67 to 68% strength nitric acid (azeotropic acid) are simultaneously added dropwise from different dropping funnels, with vigorous stirring. During this addition, a reaction temperature of 36° C. is maintained by indirectly cooling the reaction flask with ice water. After completion of the addition, the mixture is stirred for a further 60 minutes at 36° C. and the batch is then hydrolysed by allowing it to run cautiously into a flask and at the same time metering-in 1,160 g of water. During this operation the mixture heats up to about 120° C. and nitrous fumes are evolved. After completion of the dilution, the reaction mixture is cooled to 60°–70° C.

A sample is mixed with urea or amidosulphonic acid to remove dissolved nitrous fumes, is neutralised with 50% strength sodium hydroxide solution and is then analysed by high-pressure liquid chromatography.

The following were found as the main constituents of the diluted nitration mixture: 22.5% by weight of nitro-T-acid, 2.7% by weight of 1-nitronaphthalene-3,5,7-trisulphonic acid, 1.4% by weight of 1-nitronaphthalene-4,6,8-trisulphonic acid, 0.7% by weight of 1-nitronaphthalene-2,5,7-trisulphonic acid and 0.3% by weight of 2-nitronaphthalene-3,5,7-trisulphonic acid.

The yield of nitro-T-acid was 96% of theory, relative to naphthalene-1,3,6-trisulphonic acid employed.

The remainder of the dilute nitration solution was further processed in accordance with F.I.A.T., Final Report, No. 1016, page 32 to 39, by treatment with chalk, treatment with sodium carbonate, and reduction, to give T-acid, and the latter was further processed to give H-acid by fusing with sodium hydroxide. Yield: 63% of theory of H-acid, relative to naphthalene-1,3,6-trisulphonic acid.

Example 2

In a loop reactor having an empty volume of 2 m$^3$, 4,668 kg/hr of sulphonation melt which is at about 150° to 160° C., and, simultaneously, 645 kg/hr of 67.5% strength nitric acid (azeotropic acid) are metered continuously into a product mixture which has been nitrated to the extent of about 95 to 99% and which is being circulated by pumping; a reaction temperature of 35° to 40° C. is maintained in the loop reactor. The sulphonation melt was obtained by trisulphonating naphthalene in accordance with F.I.A.T., Final Report, No. 1016, page 32 to 39.

The reaction mixture which has been nitrated to the extent of about 95 to 99% then runs via an overflow into a stirred vessel to continue reacting at 35°–40° C., and from there, after a mean residence time of 20 to 25 minutes, into a further stirred vessel.

The nitration mixture is mixed with 2,229 kg/hour of water, whereupon nitrous fumes, carbon dioxide and water vapour escape, as a gas, from the reaction mixture. The reaction mixture (7,485 kg/hour) is cooled to 60°–70° C. and processed further, as described in Example 1, to give H-acid.

Yield: 64% of theory of H-acid, relative to naphthalene-1,3,6-trisulphonic acid.

What is claimed is:

1. In the process of the preparation of 8-nitro-naphthalene-1,3,6-trisulfonic acid by nitration of naphthalene-1,3,6-trisulfonic acid or mixture containing the latter with nitric acid in sulfuric acid the improvement comprising
   (a) carrying out the nitration in continuous operation in a plurality of reactors of which the first reactor is a loop reactor;
   (b) placing initially into the first reactor a nitration mixture in which naphthalene-1,3,6-trisulfonic acid has been nitrated to the extent of at least 80%;
   (c) adding to this nitration mixture simultaneously while thoroughly mixing the reaction mixture and maintaining the reaction temperature in the range from 30° to 60° C. (i) naphthalene-1,3,6-trisulfonic acid or a mixture containing the latter dissolved in sulfuric acid having a temperature between 100° C. and 200° C. and (ii) 1.0 to 1.4 mols of nitric acid per mol of naphthalene sulfonic acid in such a manner that a sulfuric acid concentration in the range of 86 to 94% by weight relative to the sum of water and sulfuric acid present is maintained during the nitration;
   (d) carrying out the nitration in the loop reactor to the extent of at least 80%;
   (e) completing the nitration reaction by transferring the nitration mixture into a series of one or two stirred reactor vessels until reaction is complete; and
   (f) then working up the completed reaction mixture in known manner.

* * * * *